United States Patent [19]

Kaiser

[11] 4,235,112
[45] Nov. 25, 1980

[54] RAIL FLAW DETECTOR POSITION CONTROL

[75] Inventor: Willard D. Kaiser, Grove City, Ohio

[73] Assignee: The United States of America as represented by the Secretary of the Department of Transportation, Washington, D.C.

[21] Appl. No.: 63,819

[22] Filed: Aug. 6, 1979

[51] Int. Cl.³ .............................................. G01N 29/04
[52] U.S. Cl. ........................................ 73/634; 73/636
[58] Field of Search ................. 73/620, 625, 634, 636, 73/641

[56] References Cited

U.S. PATENT DOCUMENTS

| | | | |
|---|---|---|---|
| 3,969,926 | 7/1976 | Walker et al. | 73/634 |
| 3,978,714 | 9/1976 | Shraiber et al. | 73/634 |
| 4,044,594 | 8/1977 | Owens et al. | 73/636 |

*Primary Examiner*—James J. Gill
*Attorney, Agent, or Firm*—Herbert E. Farmer; Harold P. Deeley, Jr.; Otto M. Wildensteiner

[57] ABSTRACT

A laterally movable ultrasound transducer, comprising the sensor of a rail fault detection device, is automatically centered on the rail as the detection device moves along the rail. The sensor includes a pair of ultrasound receiving transducers positioned to either side of a transducer which generates and receives ultrasonic energy. Signals provided by the receiving transducers are compared and any difference therebetween employed to control the lateral position of the sensor with respect to the rail.

6 Claims, 2 Drawing Figures

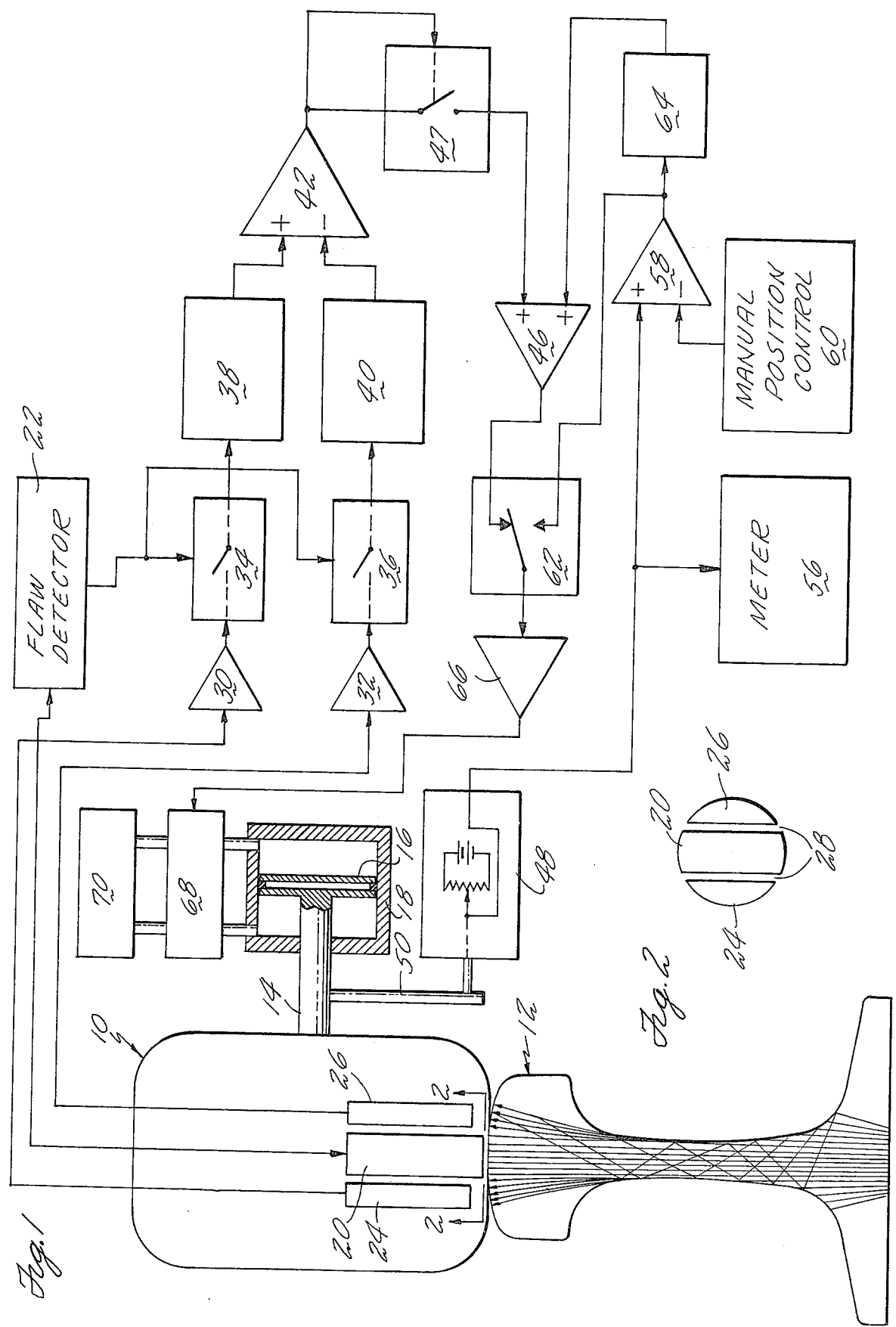

RAIL FLAW DETECTOR POSITION CONTROL

ORIGIN OF THE INVENTION

The invention described herein was made in the course of, or under, a contract with the U.S. Department of Transportation and may be manufactured and used by or for the Government for governmental purposes without the payment of any royalties thereon or therefor.

BACKGROUND OF THE INVENTION (1) Field of the Invention

The present invention relates to the inspection of elongated members a particularly to the non-destructive testing of rails of the type employed to form railroad tracks. More specifically, this invention is directed to ultrasonic rail-flaw inspection equipment suitable for continuous field testing of rails. Accordingly, the general objects of the present invention are to provide novel and improved methods and apparatus of such character.

(2) Description of the Prior Art

It is well known that safe and economic railway system operations requires the periodic inspection of rails in an effort to detect flaws. Failure to replace a rail section which has developed a flaw may result in the rail breaking which, in turn, may cause a derailment. To be feasible, rail flaw inspection equipment must be capable of continuous operation wherein equipment is moved along the test rail at a reasonable speed. Over the years, numerous non-destructive rail testing techniques have been proposed. The present state-of-the-art is represented by ultrasonic inspection apparatus such as, for example, exemplified by U.S. Pat. Nos. 3,028,751, 3,028,906, and 4,044,594.

A principal requirement for ultrasonic rail-flaw inspection equipment is that the transducer, which alternatively generates the ultrasound energy and/or receives echoes from within the object under test and converts these echoes into electrical signals, must be positioned laterally with respect to the rail so as to transmit and receive ultrasonic signals through the web of the rail. This critical position must be maintained regardless of rail curvature and wear. Accordingly, it is conventional practice to mount the ultrasonic flaw detection device transducer on a carriage which has provision to make lateral transducer adjustments with respect to each rail. While several concepts for automatic transducer carriage lateral position control have been proposed, to date none of these concepts have proved to be successful. The lack of automatic carriage position control has resulted in the average operating speed of present ultrasonic rail-flaw inspection equipment being severely limited because almost all decisions with respect to carriage position must be made by an operator who must also control the system manually. Thus, particularly when entering and leaving curves and when operating on badly worn rails, present ultrasound rail-flaw inspection equipment will either be inoperative because of lateral misalignment or the speed of testing must be reduced to an unacceptable slow rate in order to permit manual maintenance of the requisite alignment of the transducer with the rail web.

Prior proposals for automatic transducer carriage control for ultrasonic rail-flaw inspection equipment have suggested the use of sensors which reference position from outside surfaces of the rail head. This mode of operation, however, has not proven to be successful since, due to wear, the location of the exterior of the rail head does not always locate the acoustic center and coincide with the transducer located required to transmit and receive ultrasonic signals through the web of the rail. Oscillating carriage type systems have also been proposed such as, for example, the system of FIG. 8 of U.S. Pat. No. 3,028,751. These continuously oscillating systems, however, are characterized by relatively slow maximum rate of longitudinal movement and a serious lack of reliability due to the increased wear on the components of the transducer head resulting from the continuous motion.

SUMMARY OF THE INVENTION

The present invention overcomes the above briefly discussed and other deficiencies and disadvantages of the prior art by providing a novel and improved technique and system, particularly well suited for ultrasonic rail-flaw inspection, wherein a laterally movable transducer carriage is automatically positioned in such a manner as to permit comparatively high speed continuous sensing. In accordance with the present invention, a continuous analog signal proportional to any error between the transducer; i.e., the sensor position; and the center of the rail is developed and the transducer is repositioned as a function of this error signal.

Apparatus in accordance with the present invention employs a pair of specially designed ultrasonic sensors which provide input signals employed in the development of the aforementioned analog error signal. These ultrasonic sensors could be mounted in a separate rail-position sensing head but are preferably located in the same supporting medium, and in symmetrical relationship with respect to, the primary transmit-receive transducer. Since the pair of sensors employed for position control are passive; i.e., they only receive ultrasound energy; the occurrence of electrical or ultrasonic "cross talk" between the position control sensing system and the flaw inspection system is minimized. The primary ultrasound transmit-receive transducer and the pair of position control system ultrasound transducers are mounted on a carriage which travels along the rail and the head, or heads, in which the ultrasound transducers are mounted will be capable of lateral movement with respect to this carriage and the rail. The analog position error signal, which is produced through comparison of the outputs of the pair of position control ultrasonic sensors, comprises the control input for a servo system, a hydraulic position control mechanism, for example, which automatically positions the transducers.

Also in accordance with the present invention, an actual position signal preferably will be fed back to the control system in parallel with the ultrasonically derived error signal. Under normal operation, the ultrasonic signal will be much stronger than the position feedback signal and will determine the transducer head lateral position. However, should the ultrasonically derived position error signal be lost, the position feedback signal will predominate and will cause the head to move such that the primary transmit-receive transducer is driven to a manually preset position which is an estimate of the geometric center of the rail. As the primary transducer moves toward the geometric center of the rail under position feedback control, the ultrasonic signal will customarily be re-established and will regain control.

BRIEF DESCRIPTION OF THE DRAWING

The present invention may be better understood and its numerous objects and advantages will become apparent to those skilled in the art by reference to the accompanying drawing wherein like reference numbers referred to like elements in the several FIGURES and in which:

FIG. 1 is a block diagram which schematically illustrates a preferred embodiment of the present invention in the environment of rail-flaw inspection equipment; and FIG. 2 is a bottom view of the ultrasound transducers located in the movable head of the embodiment of FIG. 1.

DESCRIPTION OF THE PREFERRED EMBODIMENT

With reference now to the drawing, a transducer head is indicated generally at 10. Head 10 may, for example, be in the form of a track contacting "wheel" or sled sensor comprised of suitable means to support the transducers at the proper orientation to achieve the desired acoustic coupling of the sonic signals into the rails. The "wheel" or sled will be supported by a carriage, not shown, and will be laterally movable with respect to the carriage. The transducer head 10 will be urged against the upper surface of the head portion of a rail, indicated generally at 12, and will move with the carriage along the rail 12 in the longitudinal direction during a testing procedure. The lateral positioning of head 10 is typically accomplished by mounting the head on a mechanism or linkage connected to the extension 14 of the piston rod of a bidirectional piston 16 located within the cylinder 18 of a pneumatic or hydraulic actuator. Alternatively, lateral movement of the head 10 may be accomplished with a mechanical or electrical actuator.

Referring jointly to FIGS. 1 and 2, transducer head 10 causes three ultrasound transducers which typically will be piezoelectric crystals, lead metaniobate crystals for example, to move laterally. The primary transmit-receive transducer 20 will be an existing 0 degree flaw detection transducer of the type presently used in rail-flaw detection equipment. Transducer 20, when energized by "transmit" signals received from the flaw detection equipment 22, will generate bursts of ultrasound energy which are coupled into the rail 12. Both transducer 20 and the flaw detection equipment 22 are known in the art and thus will not be described further herein. Transducer 20 will receive echoes from within the rail 12, will transduce these echoes into electrical signals and these electrical signals will be provided as the information bearing input signals to the flaw detection equipment 22.

A pair of specially designed ultrasound sensors 24 and 26 are mounted in head 10 to either side of and symmetrically with respect to transducer 20. Transducers 24 and 26 are "passive" in that they operate in a receive mode only and are not employed for the generation of ultrasound energy. Echoes received from the base of the rail by transducers 24 and 26 are converted into electrical signals which are delivered to position control circuitry which will be described below. Transducers 24 and 26 are closely spaced to the flaw detection transducer 20, a spacing of about 0.35 inches being typical but with larger spacing preferred. The three transducer crystals are separated by acoustic barriers, indicated in FIG. 2 at 28, and the entire subassembly of the three crystals will be potted in a suitable plastic material. Although not shown in the drawing, it will be understood that all three transducers may be tuned; i.e., are electrically connected in tank circuits where there is a tuning coil connected in parallel with each crystal.

The output signals from transducers 24 and 26 are respectively applied to amplifiers 30 and 32. The outputs of amplifiers 30 and 32 are delivered, respectively via gating circuits 34 and 36, to respective peak detector circuits 38 and 40. Gating circuits 34 and 36 are controlled by an output signal provided by flaw detector 22 such that the signals passed to the peak detector circuits are commensurate with echoes returned from the base of the rail through the rail web. Restated, the "opening" of gates 34 and 36 is timed such that signals will be passed to the peak detector circuits at a point in time subsequent to the energization of the transmit-receive transducer 20; this time delay corresponding to the time it will take the ultrasound energy to travel to the base of the rail, be reflected therefrom and be received back at the surface of the rail. Gating circuits 34 and 36 may, for example, be merely electronic analog switches and the enabling signals for the gates will customarily be generated internally in flaw detector 22 by a timing circuit which produces an output pulse of preselected duration at a preselected time subsequent to transmission of an energizing signal to transducer 20. Peak detector circuits 38 and 40 may, for example, each comprise a diode-resistor-capacitor network which provides a steady state output signal commensurate with the maximum amplitude of the signals passed by gates 34 and 36.

The signals which appear at the outputs of peak detector circuits 38 and 40 are compared in a differential amplifier 42. Amplifier 42 provides an "ultrasonic" position error signal having a magnitude and polarity indicative of the difference between the signals generated by transducers 24 and 26. This error signal is normally delivered as a first input to a summing amplifier 46. An error signal from amplifier 42 of excessive magnitude may be indicative of a loss of acoustic coupling between one of the passive transducers and the rail head. Accordingly, the apparatus may include a voltage sensitive switch 47 connected between amplifiers 42 and 46 to disconnect the output of amplifier 46 under the condition of loss of coupling to one transducer. If deemed desirable, switch 47 could be made to automatically control the operation of a mode selector switch 62 which will be described below. Logic circuitry, for example a NAND gate connected to both inputs to amplifier 42, may be included in the system to provide an indication of total loss of acoustic coupling to the rail head and such indication may also be employed to automatically control the operative mode between response to the "ultrasonic" position error and response to a "geometric" position error.

In order to generate the "geometric" position error signal, which is indicative of the displacement of the center of primary transducer 20 from the geometric center of the rail, the actual lateral position of head 10 relative to its support carriage is sensed and a position feedback signal generated. Sensing of actual transducer head position is accomplished in the disclosed embodiment by mechanically coupling the piston rod extension 14 of actuator 18 to a transducer 48 which may, as schematically illustrated, comprise merely a potentiometer having its wiper arm coupled to piston rod extension 14 by means of a linkage 50. The position feedback signal from transducer 48 is delivered to a meter 56, which provides a visual indication of actual head position, and to the first input of a further differential amplifier 58. A signal commensurate with an operator selected head lateral position is supplied as the second input to amplifier 58. The manually selected command signal is generated by means of a signal generator 60 which may comprise merely a potentiometer. The output of differential amplifier 58 will, accordingly, be a "geometric" position error signal having a magnitude and polarity indicative of the deviation of the head to either side of a position corresponding to the setting of signal generator 60.

The "geometric" position error signal from differential amplifier 58 will be delivered as one of the inputs to a manually operated mode control switch 62. The "geometric" position error signal will also be delivered, via an attenuator 64, as a second input to summing amplifier 46. In the normal operating mode, the mode control switch 62 will be in the "automatic" position shown whereby the "ultrasonic" position error signal, which appears at the output of the differential amplifier 42, and a weak "geometric" position error signal will be summed and the resultant control signal delivered as the input to a current amplifier 66. When mode control switch 62 is in the manual position, the "geometric" position error signal from differential amplifier 58 will be directly delivered as the input to current amplifier 66.

The output of current amplifier 66 is applied as the drive signal to a servo valve 68. Valve 68 controls the flow, from a pressurized source 70, of fluid into the cylinder of actuator 18. Thus, the signal from amplifier 66 causes the servo valve 68 to control flow into actuator 18 to reposition the piston 16 until the error signal appearing at the input to amplifier 66 becomes small.

Continuing to discuss the normal or automatic mode of operation, the attenuator 64 causes the "geometric" position error signal from amplifier 58 to be small relative to the "ultrasonic" position error signal provided by amplifier 42. Accordingly, the position of the head 10 is primarily controlled by the "ultrasonic" position error signal. When an abnormal condition, such as oil on the track, causes the ultrasonic signal to be lost, the position error signal from amplifier 42 will become very small and the "geometric" position error signal from amplifier 58 will become the predominant error signal controlling the servo valve 68. This weak "geometric" position error signal will cause the transducer head 10 to slowly move to the geometric center of the rail as previously selected by the operator by means of the signal generator 60. When ultrasonic coupling between the transducers and track is reestablished, the "ultrasonic" position error signal will again predominate and will control the position of the transducer head 10.

For setting up and calibrating the equipment, the mode selector switch 62 is set to the manual position and the geometric position error signal is supplied directly at "high" gain from amplifier 58 to driver amplifier 66. In this mode of operation the attenuator 64 is removed from the circuit and the system responds as a normal position feedback control system. Present practice in the ultrasonic inspection of rails is to use a transducer which is approximately 0.5 inches wide and which is operated at a frequency in the range of 2.25 to 5.0 MHz. The shape of the passive transducers 24 and 26 is not critical but their relative position to each other and to the 0 degree transmit-receive transducer 20 is important. The passive transducers must be positioned on each side of the transmit-receive transducer so that a line through their centers is perpendicular to the longitudinal direction of the rail. The separation between the passive transducers is governed by the size of the 0 degree transmit-receive transducer and should be less than ½ inch. The size; i.e., the width; of the 0 degree transmit-receive transducer preferably is in the range of ⅜" to 1" to minimize beam divergence and provide efficient operation; i.e., operation with an acceptable signal-to-noise ratio. In the case of a 0 degree flow detection transducer of the type depicted in the drawing, a spread angle for the beam of ultrasonic energy of approximately 28.5° will result. Considering the dimensions of the rail, with a beam-spread angle of approximately 28.5°, the transmitted ultrasound beam will be significantly wider than the rail web and the ultrasonic energy will normally be guided by the outside surfaces of the web. The outside surfaces of the web also guide the ultrasound energy back upwardly after it has been reflected from the base of the rail. The channelizing effect of the web thus causes the maximum ultrasound energy intensity to occur near the center of the rail head with sharply decreasing intensity at locations where the spreading of the beam of ultrasound energy is prevented by the outside surfaces of the rail web. The receive transducers 24 and 26 are located in the area where the intensity is rapidly decreasing and thus any deviation of the transducer 20 from the point of maximum signal strength will, since the receive transducers are fixed in position relative to transducers 20, result in a significant imbalance in the magnitude of the signals produced by transducers 24 and 26 in response to received reflections. It is this signal imbalance, as represented by a DC error signal at the output of amplifier 42, which will cause lateral adjustment of the position of head 10. Thus, the automatic carriage control system of the present invention will cause the transducer head to move laterally to the position that produces the strongest base signal if adequate coupling between the transducers and rail is available to produce a base signal. If the rail is badly worn or very dirty, the acoustic coupling between the rail and one or both of transducers 24 and 26 may be lost and, should this happen, the system will as explained above automatically shift to control on the geometric center until either acoustic coupling is reestablished or the operator assumes manual control through the operation of mode control switch 62.

While a preferred embodiment has been shown and described, various modifications and substitutions may be made thereto without departing from the spirit and scope of the invention. Accordingly, it is to be understood that this invention has been described by way of illustration and not limitation.

What is claimed is:

1. An apparatus for ultrasonically inspecting railroad track rail elongated members for abnormalities, the apparatus including a sensor head movably supported fom a carriage so as to be in contact with the member to be inspected, the carriage being movable longitudinally along the member to be inspected and the sensor head being separately movable laterally with respect to the direction of movement of the carriage, the improvement comprising means for automatically positioning the sensor head laterally relative to the carriage comprising:

a pair of passive ultrasound transducers movably supported from the carriage, the transducers of said pair respectively being equally spaced to either side of a line through the center of an ultrasound generator in the sensor head, said line being parallel to the direction of movement of the carriage, the transducers of said pair being acoustically coupled to the member being inspected and generating electrical signals commensurate with reflected ultrasound energy;

means responsive to the electrical signals generated by the transducers of said pair for generating a position error signal commensurate with any difference between the transducer generated signals;

actuator means for imparting lateral movement to the sensor head and to said passive transducers, said actuator means being supported on the carriage; and means responsive to said position error signal for delivering a control signal to said actuator means to cause movement of said head and passive transducers in a direction to null the error signal.

2. The apparatus of claim 1 further comprising:

means for sensing the actual lateral position of the sensor head and for generating a signal commensurate with deviation of the sensor head from the geometric center of the member being inspected; and means for selectively coupling position error signals or deviation from geometric center signals to said actuator control signal delivering means.

3. The apparatus of claim 2 wherein said means for generating deviation from geometric center signals comprises:

means for sensing the actual lateral position of the sensor head and generating a signal commensurate therewith;

means for generating a signal commensurate with the center of an elongated member to be tested, the center being measured in a direction transverse to the direction of carriage movement; and means for comparing said signals commensurate with lateral position and member center to generate a deviation error signal.

4. The apparatus of claim 3 further comprising:

attenuator means, said attenuator means receiving said deviation error signal and reducing the magnitude thereof;

means for summing the reduced magnitude signal from said attenuator means with said position error signal; and means delivering the summed output signal from said summing means to said selective coupling means as a first input thereto, the other input to said selective coupling means being the unattenuated deviation error signal.

5. A method for the inspection of a railroad track steel rail comprising the steps of:

coupling an ultrasound transceiver to the rail head whereby ultrasound energy generated by the transducer will travel to the base of the rail and will be reflected back to the transducer;

ultrasonically coupling a pair of passive ultrasound transducers to the rail head respectively at points equally spaced to either side of a line through the center of the ultrasound transceiver;

moving the ultrasound transceiver and the passive ultrasound transducers longitudinally along the rail head;

periodically energizing the transceiver to couple bursts of ultrasonic energy into the rail, echoes being subsequently received by the transceiver and analyzed for discontinuities in the rail;

comparing the magnitude of the ultrasound energy received at the passive ultrasound transducers subsequent to reflection from the rail base of the bursts of ultrasonic energy; and adjusting the lateral position of the ultrasound transceiver and the passive ultrasound transducers to minimize any differences in the magnitude of the signals received at the passive ultrasound transducers, the position adjustment being performed without varying the relative positions of the transceiver and transducers.

6. The method of claim 5 further comprising the steps of:

measuring the actual lateral position of the transceiver relative to the geometric center of the rail head;

comparing the actual lateral position with a desired lateral position to determine the geometric position error; and employing the geometric position error to adjust the transceiver and transducer lateral position when acoustic coupling between either or both passive transducers and the rail head is interrupted.

* * * * *